United States Patent [19]

Lohri

[11] 4,393,243

[45] Jul. 12, 1983

[54] CAROTENOID INTERMEDIATE BY AN OXIDATION PROCESS

[75] Inventor: Bruno Lohri, Kaiseraugst, Switzerland

[73] Assignee: Hoffmann-La Roche Inc., Nutley, N.J.

[21] Appl. No.: 244,574

[22] Filed: Mar. 17, 1981

[51] Int. Cl.³ .............................................. C07C 45/34
[52] U.S. Cl. ..................................... 568/344; 568/360
[58] Field of Search ........................................... 568/344

[56] References Cited

U.S. PATENT DOCUMENTS

| | | | |
|---|---|---|---|
| 3,944,620 | 3/1976 | Becker et al. | 568/344 |
| 4,026,948 | 5/1977 | Becker et al. | 568/344 |
| 4,046,813 | 9/1977 | Brenner | 568/344 |
| 4,092,361 | 5/1978 | Costantine et al. | 568/344 |

OTHER PUBLICATIONS

Hays et al., Cam. J. Chem., vol. 43, pp. 1306–1317 (1965).

*Primary Examiner*—James H. Reamer
*Attorney, Agent, or Firm*—Jon S. Saxe; George M. Gould; Peter R. Shearer

[57] ABSTRACT

A process for synthesizing 3,5,5-trimethyl-4-[(E)-3-oxo-1-butenyl]-2-cyclohexen-1-one which is a known intermediate in a process for preparing a carotenoid.

19 Claims, No Drawings

CAROTENOID INTERMEDIATE BY AN OXIDATION PROCESS

BACKGROUND OF THE INVENTION

The compound 3,5,5-trimethyl-4-[(E)-3-oxo-1-butenyl]-2-cyclohexen-1-one, an intermediate useful for preparing cartenoids, has been manufactured by oxidizing α-ionone with t-butyl chromate [V. Prelog et al., Helv. Chim. Acta 35, 986–992 (1952)]. However, this process yields only 60% conversion within 14 days of reaction time and the yield amounts to only 25% relative to reacted α-ionone.

A catalytic oxidation process using a cobalt acetate and bromide catalyst is known for compounds containing allylic and benzylic groups [A. S. Hay et al., Can. J. Chem. 43, 1306–1317 (1965)]. Only one example is described for compounds containing allylic groups, namely the oxidation of cyclohexene to 3-acetoxycyclohexene. The product from this oxidation is effected in very low yield.

SUMMARY OF THE INVENTION

This invention is directed to a process for the manufacture of 3,5,5-trimethyl-4-[(E)-3-oxo-1-butenyl]-2-cyclohexen-1-one of formula:

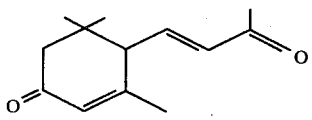

by oxidizing α-ionone of formula:

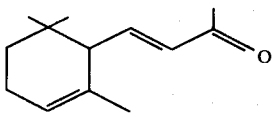

in concentrated acetic acid with oxygen or an oxygen containing gas in the presence of a cobalt acetate/bromide catalyst to provide thereby catalytic oxidation of a compound of formula II. The process provided by the invention yield predominantly as product the oxo compound of formula I. Further, the high selectivity of the oxidation in the process of the invention is surprising, since α-ionone has three allylic centers and, can undergo an allyl rearrangement to react with oxygen at four positions. The yield of directly crystallized 95% product amounts up to about 30% and the chemical yield amounts up to about 40% relative to α-ionone used. Moreover, the process provided by the present invention can be readily used on a technical scale. The process of the invention is useful in producing cartenoids.

DETAILED DESCRIPTION OF THE INVENTION

In accordance with this invention a process is provided for synthesizing 3,5,5-trimethyl-4-[(E)-3-oxo-1-butenyl]-2-cyclohexen-1-one of formula I. The compound of formula I is produced by oxidizing α-ionone of formula II in concentrated acetic acid with oxygen or an oxygen containing gas in the presence of a cobalt acetate/bromide catalyst.

The conversion of α-ionone into 3-oxo-α-ionone of formula I is carried out in an oxidation reaction mixture in accordance with this invention as a homogeneous catalytic oxidation in concentrated acetic acid. The catalyst used is a cobalt acetate/bromide catalyst [as described, for example, in Can. J. Chem. 43, 1306–1317 (1965)] and the oxidizing agent used is an oxygen containing gas or oxygen.

The catalyst may be prepared by any acceptable procedure recognized in the art from cobalt acetate and a bromide ion-forming substance which preferably is soluble in the oxidation reaction mixture, and may be prepared directly in the reaction vessel in which the oxidation is carried out. It is especially preferred that the cobalt acetate be in the hydrated form, such as cobalt acetate tetrahydrate which is most especially preferred.

The bromide ion-forming substance of the catalyst used in this invention may be selected from any substance capable of producing bromide ions in the oxidation reaction mixture. Among the bromide ion-forming substances that may be employed for this purpose in the reaction mixtures used in the invention are ones such as for example acetyl bromide, hydrogen bromide, sodium bromide or ammonium bromide, with ammonium bromide being preferred.

The amount of cobalt salt used in carrying out the process of this invention may be any amount conventionally used in catalysis of the art. Said amount is preferably based on the concentration of α-ionone used in the reaction and is conveniently an amount of at least about 10 mole percent, preferably in an amount of about 20 mole percent, based on the α-ionone concentration in the reaction mixture. The ratio of cobalt salt to the bromide ion-forming substance is not critical and can be in any suitable ratio recognized in the art. The bromide to cobalt molar ratio conveniently amounts to at least about 0.5:1 and preferably about 1:1.

Concentrated acetic acid is used as the solvent in the process provided by the present invention. The term "concentrated acetic acid" in the scope of the present invention means that the total water concentration of the oxidation mixture (including the water of crystallization when cobalt acetate tetrahydrate is used) at the beginning of the oxidation does not amount to more than about 2 weight percent. The oxidation is preferably carried out with at most about 1 and especially preferably with at most about 0.7 weight percent of water. The concentrated acetic acid is preferably glacial acetic acid which is anhydrous acetic acid. The concentrated acetic acid may be used as a solvent in the absence of other solvents but it is conveniently used in the form of a mixture with another solvent.

If desired other solvents may be used in mixture with the concentrated acetic acid. The other solvent used in mixture with the acetic acid may be any inert organic solvent such as for example ketones, esters, dioxan, saturated hydrocarbons, inert aromatic solvents and the like. Examples of such inert organic solvents are acetone, ethyl methyl ketone, diethyl ketone, ethyl acetate, isopropyl acetate, n-butyl acetate, cyclohexane, hexane, benzene and chlorobenzene. The preferred inert organic solvent for admixture with acetic acid are ketones and, especially, esters and cyclohexane. Cyclohexane is particularly preferred.

The oxidation is therefore preferably carried out in a mixture of glacial acetic acid and cyclohexane. The optimum volume ratio of the solvent components depends on the type of components used as recognized in the art. For example, the optimum volume ratio amounts to about 1:1 in the case of glacial acetic acid and cyclohexane.

The addition of water to the oxidation reaction mixture while carrying out the process of this invention may be necessary in order to facilitate the solubility of the catalyst and thereby improve the catalytic effect. Where water is not added to the reaction mixture the catalyst may separate out of the mixture during the oxidation in some cases. For example, it is preferred that water is added (about 0.4% by weight of the reaction mixture) when glacial ac etic acid and ethyl acetate in a ratio of 1:1 and cobalt acetate tetrahydrate are used, preventing thereby the catalyst from separating out during the oxidation.

The amount of water used to facilitate the solubility of the catalyst during the oxidation reaction is not critical in carrying out the process of this invention, but too large an amount of water in the reaction may significantly slow down the oxidation. The minimum amount necessary to provide and to maintain solubility of the catalyst is all that is needed and may be determined by conventional means employed in the art. An amount of water in a concentration of up to about 2% by weight of the reaction mixture is preferred. It is most preferred that the concentration of water not be more than about 0.7% by weight of the reaction mixture.

In accordance with this invention the oxidizing agent used to carry out the oxidation in the oxidation reaction mixture is either oxygen or an oxygen-containing gas.

The term "oxygen-containing gas" signifies generally a mixture of oxygen and any inert gas. For example, the oxygen containing gas may be conveniently a nitrogen/oxygen mixture (e.g. air). The ratio by weight of oxygen to the inert gas in the oxygen-containing gas is not critical. It is preferred however that the amount of oxygen lies between about 10 percent and about 50 percent, preferably between about 20 percent and about 40 percent, by volume respectively. If the oxidation is carried out in a closed system, then for the most part the lower inert gas concentrations are conveniently used.

The oxidizing agent may be supplied to the oxidation reaction mixture during the reaction by any conventional means known in the art. For example the oxidizing agent may be bubbled through the reaction mixture as by conventional inert tubing recognized in the art as suitable for carrying out an oxidation reaction.

Temperature and pressure for carrying out the oxidation reaction of this invention is not critical and can be any temperature and pressure recognized in the art as suitable for oxidation, given the particular solvent being used. The oxidation is preferably carried out at atmospheric pressure and a temperature of about 30° C. to about 80° C., with the maximum temperature preferably being the reflux temperature of the reaction mixture. A noticeable slowing-down of the oxidation may occur in certain cases at temperatures close to the reflux temperature. The oxidation is most preferably carried out at a temperature of about 35° C. to about 65° C., especially preferably at about 40° C. to about 55° C. A temperature of about 45° C. to about 50° C. is particularly especially preferred.

In a typical procedure for this invention, the catalyst is introduced into a reaction vessel and treated with acetic acid and an inert organic solvent, providing thereby a mixture which is heated conventionally with stirring. The oxidizing agent is introduced into the mixture conventionally and continuously during the reaction process, with the addition of α-ionone of formula II after the initial introduction of the oxidizing agent. The reaction is allowed to proceed until the oxidation is completed as determined by any art recognized method, with the formation of the 3-oxo-α-ionone of formula I as product. Thereafter the product may be isolated and crystallized by procedures recognized in the art.

After completion of the oxidation, for example, the oxidation mixture can be freed from solvent in vacuo, the residue treated with ice, neutralized, for example with sodium hydroxide, to a pH-value of about 6.5 and the product extracted (e.g. with ether). Crystallization of the product can be brought about by initially treating the product extract with silica gel. After filtration and evaporation of the solvent, crystallization can be carried out, for example, from an ether/hexane mixture. In this manner crystalline, about 95% pure 3-oxo-α-ionone of formula I, can be obtained in yields of up to about 30% by weight. The yield can be increased by chromatography of the mother liquor. When the oxidation is carried out using acetic acid alone as the solvent the 3-oxo-α-ionone can not be crystallized directly because of the high amounts of acetoxy compounds present. However, in such cases it can be isolated by chromatography.

The product obtained by the process of this invention is a 3-oxo-α-ionone of formula I which is a known intermediate in a process for preparing a carotenoid. The conversion of a compound of formula I into a cartenoid can be accomplished by utilizing procedures well known in the art such as for example the procedure disclosed in B. C. L. Weedon, J. Pure and Appl. Chem. 47, 161–171 (1976).

The following Examples further illustrate the present invention but are not meant to restrict the invention in scope or spirit:

EXAMPLE 1

10.4 g (41.6 mmol) of cobalt acetate tetrahydrate and 4.0 g (41.6 mmol) of ammonium bromide are introduced into a 750 ml sulphonation flask and treated with 240 ml of glacial acetic and 240 ml of cyclohexane. This resulting mixture is heated to 50° C. in an oil-bath while stirring and introducing 35% oxygen. About 10 minutes after attaining this temperature there is added in one portion to the deep-blue solution (the blue color indicates the formation of the catalytically active cobalt acetate/bromide complex) 40 g (208 mmol) of 98% α-ionone. The oxidation is complete after 4–5 hours. The mixture is concentrated extensively at 50° C. in a water-jet vacuum and the resulting residue is mixed with 50 g of ice and 50 ml of water. The resulting aqueous emulsion is adjusted to pH 6–6.5 with about 25 ml of 10% sodium hydroxide and then extracted with two 150 ml portions of ether. The organic phases are obtained and combined, washed with two 50 ml portions of water, dried over magnesium sulphate and treated with 40 g of silica gel. The resulting suspension is stirred at room temperature for 3 hours and subsequently the silica gel is filtered off and washed with 200 ml of ether. The filtrate is evaporated and the residue (about 38 g) is crystallized from ether/hexane. Crystallization gives 13.4 g (30%) of 95% 3,5,5-trimethyl-4-[(E)-3-oxo-1-butenyl]-2-cyclohexen-1-one(3-oxo-α-ionone) as light yellowish crystals of melting point 74.5°–76° C.

EXAMPLE 2

Items 1–6 given in Table 1 hereinafter are carried out following the procedure of Example 1 substituting therein 5 g of 92% α-ionone for the 40 g of 98% α-ionone, 1.3 g (20 mol percent) of cobalt acetate tetrahydrate for the 10.4 g, and 0.7 g, (27 mol percent) of ammonium bromide for the 4.0 g. The amount of solvent substituting for glacial acetic acid and cyclohexane is represented in Table 1 and amounts to 60 ml. The yields of 3,5,5-trimethyl-4-[(E)-3-oxo-1-butenyl]-2-cyclohexen-1-one (3-oxo-α-ionone) are determined by gas chromatography (GC). It will be observed that the sum of all products appearing in the gas chromatogram only amounts to a maximum of about 60% of the total weight. The remainder probably consists of oligomeric by-products. The oxidation conditions are not optimized.

TABLE 1

| Item | O₂ Concentration by volume | Solvent volume ratio | Oxidation time | Yield[1] |
|---|---|---|---|---|
| 1 | 12% | Glacial acetic acid/diethyl ketone (1:1) | 16 hours | 39% |
| 2 | 21% (air) | Glacial acetic acid/diethyl ketone (1:1) | 10 hours | 48% |
| 3 | 38% | Glacial acetic acid/ethyl acetate (1:2) | 10 hours | 54% |
| 4 | 100% | Glacial acetic acid/ethyl acetate (1:2) | 7.75 hours | 45% |
| 5 | 21% (air) | Glacial acetic acid/cyclohexane (1:1) | 4 hours | 53% |
| 6 | 52% | Glacial acetic acid/cyclohexane (1:1) | 2.5 hours | 48% |

[1]GC area percent

EXAMPLE 3

Items 1–3 given in Table 2 hereinafter are carried in accordance with the procedure of Example 1 substituting therein 5 g of 92% α-ionone for the 40 g of 98% α-ionone and 60 ml of glacial acetic acid/cyclohexane (1:1) for 240 ml of each, with 20 mol percent of cobalt acetate tetrahydrate for 10.4 g, 30–35% of oxygen for 35% and varying amounts of ammonium bromide as indicated in Table 2 for the 4 g. The oxidation time amounts to 6 hours. The yields of 3,5,5-trimethyl-4-[(E)-3-oxo-1-butenyl]-2-cyclohexen-1-one (3-oxo-α-ionone) are determined by gas chromatography. The sum of all products appearing in the gas chromatogram amounts to a maximum of only about 60% of the total weight. The remainder probably consists of oligomeric by-products. The oxidation conditions are not optimized.

TABLE 2

| Item | Molar ratio NH₄Br/Co(OCOCH₃)₂·4H₂O | Yield[1] |
|---|---|---|
| 1 | 1.7 | 54% |
| 2 | 1.0 | 54% |
| 3 | 0.6 | 45% |

[1]GC area percent

I claim:

1. A process for the manufacture of 3,5,5-trimethyl-4-[(E)-3-oxo-1-butenyl]-2-cyclohexen-1-one of the formula

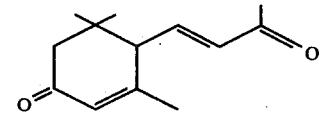

which process comprises oxidizing α-ionone of the formula

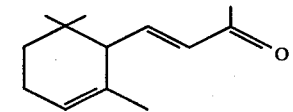

in a reaction mixture containing concentrated acetic acid with oxygen or an oxygen-containing gas in the presence of a cobalt acetate/bromide catalyst.

2. A process according to claim 1, wherein the reaction mixture contains at most about 1 weight percent of water.

3. A process according to claim 1, wherein the reaction mixture contains at most about 0.7 weight percent of water.

4. A process according to claim 1, wherein the acetic acid is glacial acetic acid.

5. A process according to claim 1, wherein the reaction mixture further contains an inert organic-solvent.

6. A process according to claim 5, wherein the inert organic solvent is selected from the group consisting of a ketone, an ester, dioxan, a saturated hydrocarbon and an inert aromatic solvent.

7. A process according to claim 6, wherein the inert organic solvent is acetone, ethyl methyl ketone, diethyl ketone, ethyl acetate, isopropyl acetate, n-butyl acetate or cyclohexane.

8. A process according to claim 7, wherein the inert organic solvent is cyclohexane and the cyclohexane/acetic acid volume ratio is about 1:1.

9. A process according to claim 1, wherein the bromide ion-forming substance is selected from a group consisting of acetyl bromide, hydrogen bromide, sodium bromide and ammonium bromide.

10. A process according to claim 1 wherein the cobalt salt to bromide ion-forming substance is in a molar ratio of at least about 0.5:1.

11. A process according to claim 10, wherein said ratio is about 1:1.

12. A process according to claim 1, wherein the cobalt acetate is in an amount of at least about 10 mole percent of the α-ionone concentration.

13. A process according to claim 12, wherein said mole percent is 20.

14. A process according to claim 1, wherein the oxygen-containing gas is an oxygen and nitrogen mixture which contains about 10 percent to about 50 percent by volume oxygen.

15. A process according to claim 14, wherein said mixture contains about 20 percent to about 40 percent oxygen by volume.

16. A process according to claim 1, wherein the oxidation is carried out at a temperature of about 30° C. to about 80° C.

17. A process according to claim 1, wherein the oxidation is carried out at a temperature of at most the reflux temperature of the reaction mixture.

18. A process according to claim 16, wherein the oxidation is carried out at a temperature of about 35° C. to about 65° C.

19. A process according to claim 18, wherein the temperature is about 40° C. to about 55° C.

* * * * *